United States Patent
Schliephake et al.

(10) Patent No.: US 6,348,638 B1
(45) Date of Patent: Feb. 19, 2002

(54) METHOD FOR REMOVING BY-PRODUCTS OBTAINED WHEN PRODUCING ACRYLIC ACID OR METHACRYLIC ACIDS

(75) Inventors: Volker Schliephake, Schifferstadt; Ulrich Hammon, Mannheim; Wolfgang Pies, Frankenthal; Ulrich Rauh, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/147,416

(22) PCT Filed: Jun. 19, 1997

(86) PCT No.: PCT/EP97/03216

§ 371 Date: Dec. 21, 1998

§ 102(e) Date: Dec. 21, 1998

(87) PCT Pub. No.: WO97/48669

PCT Pub. Date: Dec. 24, 1997

(30) Foreign Application Priority Data

Jun. 20, 1996 (DE) .......................... 196 24 674

(51) Int. Cl.⁷ .................................................. A62D 3/00
(52) U.S. Cl. ...................................... 588/205; 588/216
(58) Field of Search ................................ 562/600, 545, 562/547; 423/245.3; 588/216, 205

(56) References Cited

U.S. PATENT DOCUMENTS

| | | | |
|---|---|---|---|
| 3,198,750 A | 8/1965 | Callahan et al. ............ 568/477 |
| 3,736,355 A | 5/1973 | Croci et al. ................. 562/547 |
| 3,798,264 A | 3/1974 | Kubota et al. .............. 562/608 |
| 3,865,873 A | 2/1975 | Oda et al. ................... 562/532 |
| 3,932,500 A | 1/1976 | Duembgen et al. ......... 562/600 |
| 3,962,074 A | 6/1976 | Schropp ..................... 210/634 |
| 4,110,370 A | 8/1978 | Engelbach et al. ......... 562/545 |
| 4,224,187 A | 9/1980 | Vanderspurt ................ 502/212 |
| 4,255,590 A | 3/1981 | Allen .......................... 562/416 |
| 4,463,691 A | * 8/1984 | Meenan et al. ............. 588/209 |
| 4,618,709 A | * 10/1986 | Sada et al. .................. 562/600 |
| 4,769,218 A | 9/1988 | Leichnitz et al. ........... 422/117 |
| 4,925,981 A | * 5/1990 | Shimizu et al. ............. 562/600 |
| 5,005,493 A | 4/1991 | Gitman ....................... 110/246 |
| 5,426,221 A | 6/1995 | Willersinn .................. 560/600 |

FOREIGN PATENT DOCUMENTS

DE  1 205 502  6/1966

(List continued on next page.)

OTHER PUBLICATIONS

Kirk–Othmer, Encyclopedia of Chemical Technology, Third Edition, vol. 13, John Wiley & Sons, New York, 1989, pp. 182–206.

Primary Examiner—Steven P. Griffin
Assistant Examiner—Eileen E. Nave
(74) Attorney, Agent, or Firm—Oblon, Spivak, McClelland, Maier & Neustdt, P.C.

(57) ABSTRACT

In a process for the disposal of low, mediun, and high-boiling secondary components formed during the preparation of (meth)acrylic acid the gaseous low-boiling secondary components are burned, whilst low-boiling and medium-boiling secondary components that are dissolved in water optionally together with high-boiling secondary components treated with solvent are added.

21 Claims, 2 Drawing Sheets

FOREIGN PATENT DOCUMENTS

| | | |
|---|---|---|
| DE | 1 962 431 | 6/1970 |
| DE | 2 164 767 | 7/1972 |
| DE | 2 136 396 | 2/1973 |
| DE | 2 251 364 | 5/1973 |
| DE | 23 23 328 | 11/1974 |
| DE | 24 49 780 | 4/1976 |
| DE | 29 43 707 | 5/1980 |
| DE | 34 29 391 | 2/1985 |
| DE | 43 08 087 | 9/1994 |
| EP | 0 117 146 | 8/1984 |
| EP | 0 253 409 | 1/1988 |
| EP | 0 257 565 | 3/1988 |
| EP | 0 293 224 | 11/1988 |
| EP | 0 551 111 | 7/1993 |
| FR | 2722868 A1 | 1/1996 |
| GB | 1 450 986 | 9/1976 |
| GB | 2 146 636 | 4/1985 |
| JP | 48-91013 | 11/1973 |
| JP | 58-140039 | 8/1983 |
| JP | 59-013746 * | 1/1984 |
| JP | 59-042340 * | 3/1984 |
| JP | 1-124766 | 5/1989 |
| JP | 7-118766 | 5/1995 |
| JP | 7-118966 | 5/1995 |
| JP | 7-118968 | 5/1995 |
| JP | 7-241885 | 9/1995 |

\* cited by examiner

METHOD FOR REMOVING BY-PRODUCTS OBTAINED WHEN PRODUCING ACRYLIC ACID OR METHACRYLIC ACIDS

BACKGROUND OF THE INVENTION

1. Field of the Invention

The present invention relates to a process for the disposal of low, medium, and high-boiling secondary components formed during the preparation of (meth)acrylic acid.

2. Description of the Background

Acrylic acid is an important basic chemical. By reason of its very reactive double bond and also its acid function it is particularly suitable for use as a monomer for the preparation of polymers. Most of the monomeric acrylic acid prepared is esterified to, say, adhesives, dispersions, or varnishes prior to polymerization. Only a small portion of the monomeric acrylic acid that is prepared is directly polymerized—to, say, "super absorbers". Whereas monomers of high purity are generally required in the direct polymerization of acrylic acid, the purity requirements of acrylic acid are not so high if it is esterified prior to the polymerization.

It is well known that acrylic acid can be prepared in two stages via acrolein at temperatures ranging from 200° C. to 400° C. by heterogeneously catalyzed gas phase oxidation of propane using molecular oxygen over catalysts existing in the solid state (cf, eg, DE-A-1 962 431, DE-A-2 943 707, DE-C-1 205 502, EP-A-0 257 565, EP-A-0 253 409, DE-A-2 251 364, EP-A-0 117 146, GB-B-1 450 986 and EP-A-0 293 224). In this case oxidic multicomponent catalysts are used, eg, those based on oxides of the elements molybdenum, chromium, vanadium, or tellurium.

DE-C-2 136 396 reveals that it is possible to separate the acrylic acid from the reaction gases obtained in the catalytic oxidation of propane or acrolein by countercurrent absorption with a mixture of 75 wt % of diphenyl ether and 25 wt % of diphenyl. Furthermore DE-A-2 449 780 reveals the method of cooling the hot reaction gas by partially evaporating the solvent in a direct condenser (quenching apparatus) prior to countercurrent absorption. A problem arising here and in other process steps is the occurrence of solid materials in the apparatus, which reduces the availability of the plant. As stated in DE-A4 308 087 the amount of this solid material can be reduced by adding a polar solvent such as dimethylphthalate to the relatively nonpolar solvent mixture of diphenyl ether and diphenyl. (diphyl) in an amount of from 0.1 to 25 wt %.

Other principles of process exist besides the aforementioned absorption of reaction product containing the acrylic acid into a high-boiling solution (mixture). The aforementioned process differs from the other processes in that here the acrylic acid is absorbed into a high-boiling solution (mixture) in as anhydrous a state as possible. The water is removed from the process in a separate, process stage. The other processes provide for the complete condensation of acrylic acid and the water of reaction also formed during the catalytic oxidation. In such a case there is formed an aqueous acrylic acid solution which can be further purified via a distillation step using an agent capable of forming an azeotrope with acrylic acid (cf DE-C-3 429 391, JP-A-1 124 766, JP-A-7 118 766, JP-A-7 118 966, JP-A-7 118 968, and JP-A-7 241 885), or via an extraction stage (cf DE-A-2 164 767, JP-A-5 8140 039, and JP-A-4 8091 013). In EP-A-0 551 111 the mixture of acrylic acid and by-products that is prepared by means of catalytic gas phase oxidation is contacted with water in an absorption tower and the aqueous solution that is obtained is distilled in the presence of a solvent capable of forming an azeotrope with polar low-boilers such as water or acetic acid. DE-C-2 323 328 describes the separation of acrylic acid from an aqueous effluent liquor produced in the esterification of acrylic acid or an aqueous acrylic acid solution as is formed in the preparation of acrylic acid by oxidation of propene or acrolein, by extraction with a specific mixture of organic solvents.

A fact common to all processes that are industrially used for the preparation of acrylic acid or methacrylic acid is that any low, medium, and highboiling fractions produced consitute undesirable secondary components and thus streams of material that must be disposed of. These, at least three, streams of material represent a considerable cost-load for the process.

SUMMARY OF THE INVENTION

Thus it is an object of the present invention to provide a disposal process which solves the by-product problem relating to the production of (meth)acrylic acid economically and ecologically to optimum effect.

DETAILED DESCRIPTION OF THE REFERRED EMBODIMENTS

We have found, surprisingly, that this problem can be solved by burning the gaseous low-boilers together with the aqueous liquid stream of material comprising water-soluble low-boilers and/or medium-boilers, the high-boilers being optionally burnt with them.

Thus the invention relates to a process for the disposal of low, medium, and high-boiling secondary components that are formed during the production of (meth) acrylic acid in which gaseous readily volatile secondary components (1) are burned, low or medium-boiling secondary components (2) that are dissolved in water being added optionally together with high-boiling secondary components (3) treated with low-viscosity solvent the burning advantageously takes place in a combustion chamber equipped with one or more support gas burners, nozzle burners, or multi-fuel burners, eg, a flame evaporating burner.

In one embodiment the invention relates to a process in which the acrylic acid or methacrylic acid is prepared by
 (a) catalytic gas phase oxidation of propene or isobutene and/or acrolein or methacrolein,
 (b) absorption of the reaction product that is formed in stage (a) into a high-boiling solvent and
 (c) separation of acrylic acid or methacrylic acid from the loaded solvent from stage (b), by distillation,
where, prior to the absorption in stage (b), a portion of the solvent is evaporate d and a portion of the remaining liquid solvent is disposed of, optionally following further solvent evaporation, as high-boiling secondary component (3), and unabsorbed reaction product remaining after the absorption of the reaction product in stage (b) is cooled,
where the aqueous condensate that is obtained, optionally following subsequent extraction, is disposed of as secondary component (2) and at least a portion of the gas stream that is obtained is disposed of as secondary component (1).

Preferred embodiments of the invention are defined in the sub-claims. Other and preferred features are shown in FIGS. 1 and 2 and are described below.

In the present description, the terms highboilers, medium boilers and low-boilers and also corresponding adjectival terms denote compounds possessing a higher boiling point than acrylic acid or methacrylic acid (high-boilers) or those possessing approximately the same boiling point as acrylic acid or methacrylic acid (medium boilers) or those possessing a lower boiling point (low-boilers).

Figure 1:
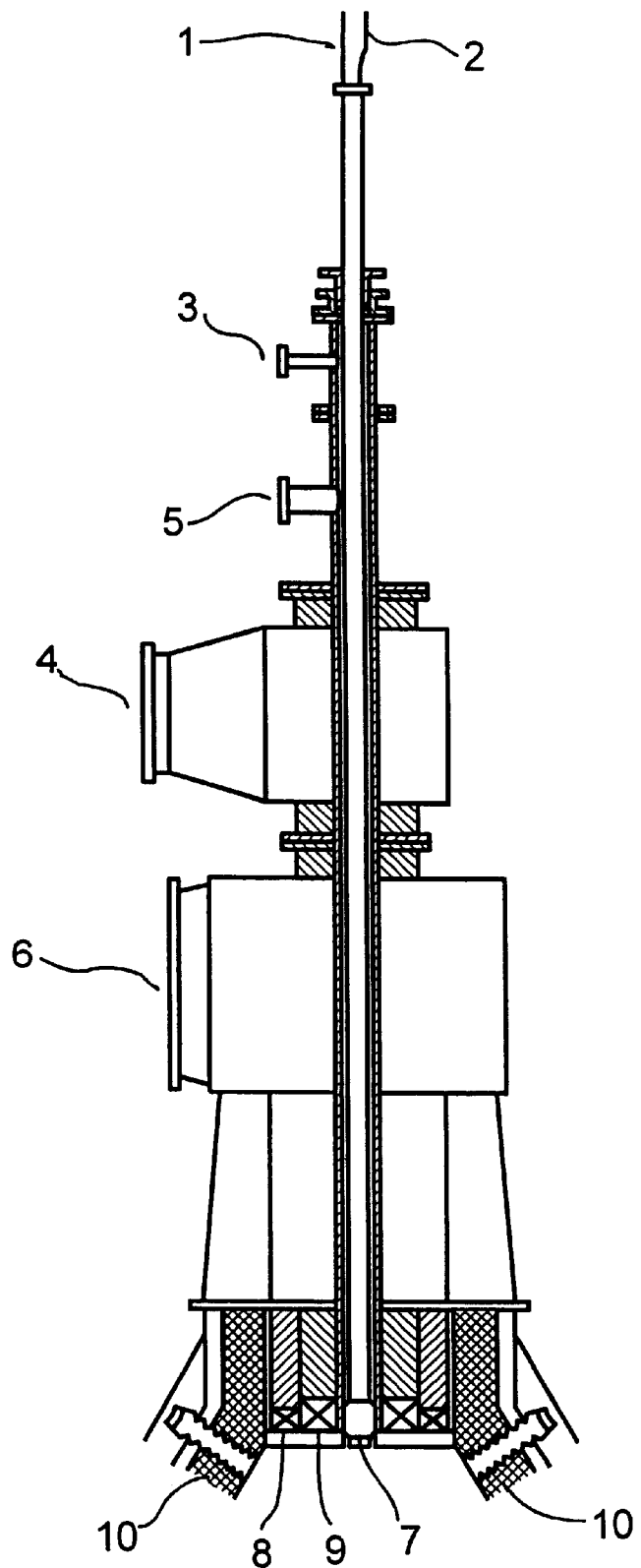
FIG. 1 is a diagrammatic illustration of a flame evaporating burner that is preferably used when carrying out the process of the invention.

The gaseous low-boiling secondary components (1), which comprise (a) gaseous secondary components that are formed during the acid preparation and (b) liquid components boiling at a low temperature (room temperature), substantially contain in addition to inert gases, such as nitrogen, water, carbon monoxide, and carbon dioxide, the low-boiling fraction of the materials that are to be disposed of, preferably acrolein, acetaldehyde, propane, propene, formaldehyde, formic acid, and/or educts that are not converted during the preparation of the (meth)acrylic acid. This stream (1) is advantageously burned in a combustion chamber. Such a combustion chamber can either be assigned to the (meth)acrylic acid production plant alone or be operated in association with other plants. An example of a flame evaporating burner that is preferably used is shown in FIG. 1 described in greater detail below.

The low or medium-boiling secondary components (2) that are dissolved in water and are to be disposed of preferably contain from 0.1 to 10 wt % of acetic acid, from 0.01 to 5 wt % of maleic acid, from 0.01 to 8 wt % of fumaric acid, from 0.2 to 4 wt % of formaldehyde, and/or from 0.1 to 10 and preferably 5 wt % of other organic material such as formic acid, propionic acid, benzaldehyde, diacrylic acid, hydroxypropionic acid, benzoic acid, and/or diphenyl ether (residues thereof, when used as solvent(s)), based, in each case, on 100 wt % of the secondary components (2). These secondary components predominantly contain acetic acid, maleic acid, and formaldehyde. This stream of secondary components (2) is added and preferably injected as an aqueous stream of material during the stage involving burning of the low-boiling secondary components (1). In an advantage ous embodiment of the invention this injecting process takes place via concentric multi-fuel nozzles, as known in the prior art. This aqueous stream containing the secondary components (2) is advantageously preconcentrated as far as possible, eg, by evaporation. To this end, the beat generated in the production process can be advantageously used to improve energy-untilization. Suitable apparatus comprises commercially available evaporators.

The high-boiling secondary components (3) predominantly contain polymers of acrylic acid or methacrylic acid, unconsumed production stabilizers, eg, phenothiazine, or p-nitrosophenol, inhibitors, eg, methylene blue, and/or the thermal degradation products thereof.

This stream of solid high-boilers (3) is advantageously first pretreated, since its physicochemical properties make it difficult to handle. Thus the solidifying point is generally so high that this stream of material is not pumpable at usual ambient temperatures. Blending with solvents which are of low viscosity at ambient temperature (viscosity usually from $0.5 \cdot 10^3$ to $2 \cdot 10^3$ Pa·s) and preferably having a high boiling point, ie from 100° to 250° C., can cause the solidifying point to drop to such an extent that the mixture becomes pumpable. The following have given particularly good results in this context: acetone, dimethyl formamide (DMF), or alcohols, particularly $C_3$–$C_{10}$ diols and/or triols, such as pentane diol, hexane diol, glycerol, glycol, dimethyl glycol, monomethyl glycol, monoethyl glycol, diethyl glycol, or mixtures thereof. The stream of secondary components (3) treated with such low-viscosity diluents can be fed to the burning process of the invention, which feed takes place separately from the other streams of secondary components (1) and (2). Preferably, the secondary components (2) and (3) are separately injected. On the other hand it is also possible to transfer the high-boiling secondary components (3), following appropriate purification, to an industrial incinerator, such as a decentral on-site incinerator, where they are comparable, in their burning properties, to heavy heating oil, or to feed them to some other processing plant.

FIG. 1 shows a cross-section of a burner preferably used on execution of the process of the invention, this being a flame evaporating burner. The essential parts of this burner are provided with reference marks. In this case the reference numerals 1 to 5 denote conduits as follows: conduit 1 for waste water, conduit 2 for atomizing steam for the waste water, conduit 3 for liquid or gaseous (eg natural gas and/or CO) supplementary fuel, conduit 4 for the stream of secondary components (2) and conduit 5 for support gas, such as natal gas. Air for combustion is introduced via the conduit 6. The stream of secondary components (1) is added separately to the air introduced. The stream of secondary components is added separately to the air for combustion, in order to avoid an explosion. The liquid components are sprayed into the combustion chamber via the nozzle 7. Reference numeral 8 and 9 denote swirl rings, which serve for air guidance or waste gas guidance, respectively. Reference numeral 10 designates flame-resistant insulating material. The nozzle 7 can be a known concentric multi-fuel nozzle, which exhibits a plurality of central annular feed gaps suitable for the feed of the stream of secondary components (2), nebulizing steam for this stream of secondary components, and also for the other components mentioned above. Thus all components are passed in through the nozzle with the exception of the air for combustion and the stream of secondary components (1). If the stream of secondary components (3) (in a form which can be handled) is also to be injected, the nozzle 7 must have a further central annular feed gap.

The actual combustion takes place in a combustion chamber (not shown) at adiabatic temperatures of cumbustion of from 800° C. to 120° C., preferably from 800 to 1000° C. In FIG. 1 the combustion chamber, the beginning of which is indicated by the flame-resistant insulating material 10, to the left of nozzle 7. The combustion chamber is advantageous associated either with the (meth)acrylic acid production plant alone, or it is operated in association with other plants. The energy liberated here can be recovered in a waste heat section which is separate from the combustion chamber advantageously, eg, in the form of high-pressure steam the combustion gases are passed through the waste heat section advantageously in such a maimer that the temperatures decrease progressively upwards. The gases thus usually arrive at the waste heat section at a temperature of cumbustion of from 850° C. to 100° C., preferably approximately 860° C., and then give off some of their energy, by cooling, to heat exchangers, which serve to recover the energy. The temperature at the outlet of the waste heat section is then approximately 200° C. The aqueous stream of material that is injected and which contains the secondary components (2) the form of energy. For this reason it is also advantageous to preconcentrate this stream as far as possible. The waste heat that is produced during combustion is advantageous used for generation of vapor, eg, steam.

The acrylic acid or methacrylic acid is usually prepared by catalytic gas phase oxidation of propene or isobutene and/or acrolein or methacrolein, followed by absorption of the reaction product that is produced during the oxidation into a low-boiling solvent, preferably water, or a high-boiling solvent followed by separation of acrylic acid or methacrylic acid by distillation and/or extraction. On the other hand it is also possible to condense the gaseous reaction product that is produced during the oxidation, which contains water, an aqueous solution of acrylic or methacrylic acid being obtained, of which the acrylic acid or methacrylic acid is in turn separated by distillation and/or extraction.

Figure 2:
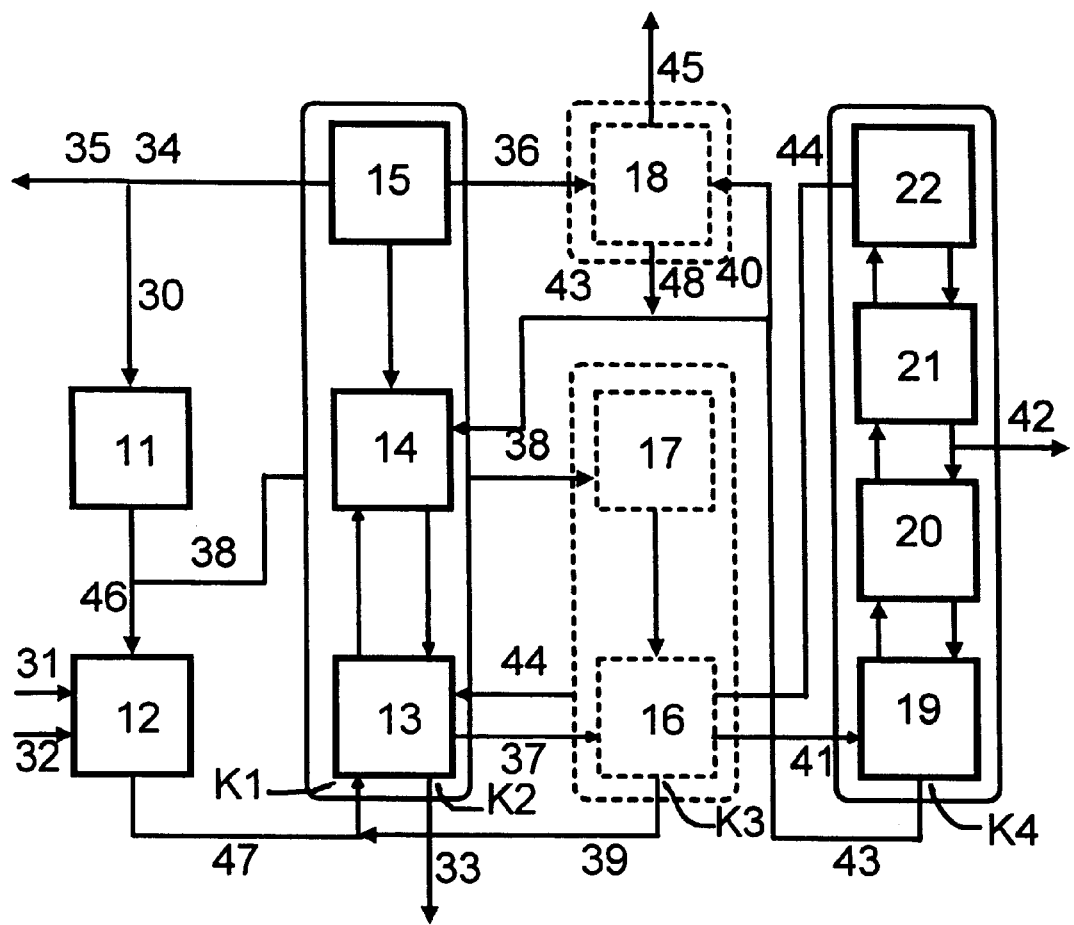
FIG. 2 shows a flow sheet for the preparation of acrylic acid.

In a preferred embodiment the invention relates to a process in which the stages (a) bis (c) are defined as above. These single stages are described below for acrylic acid. They apply analogously to methacrylic acid, unless otherwise stated. A suitable flow sheet, which shows the stages (a) to (c) and also the streams of secondary components (1) to (3) to be disposed of, is contaied in FIG. 2. In FIG. 2, reference numerals 11 to 22 refer to process, numerals 30 to 48 refer to conduits, and K1 to K4 refer to different columns/apparatus.

Stage a

Stage (a) comprises the single-stage or two-stage catalytic gas-phase reaction of propene and/or acrolein with molecular oxygen to produce acrylic acid. In the case of methacrylic acid there takes place in a similar manner a gas-phase reaction of isobutene and/or methacrolein with molecular oxygen. The gas-phase reaction can take place by known processes, particular those described in the aforementioned references. Advantageously the process is carried out at temperatures ranging from 200° C. to 500° C. The heterogeneous catalysts used are preferably oxidic multicomponent catalysts based on the oxides of molybdenum, chromium, vanadium and/or tellurium. Fur- thermore, it is also possible to prepare methacrylic acid in two stages by (1) condensation of propionaldehyde mit formaldehyde (in the presence of a secondary amine acting as catalyst) to form methacrolein followed by (2) oxidation of methacrolein to methacrylic acid.

According to the preferred embodiment that is shown in FIG. 2, following the compression 11 of the circulated gas from conduit 30, which substantial consists of nitrogen, carbon oxides and unconverted educts, this is fed by means of conduit 46, together with propene from conduit 31 and air from conduit 32, to a reactor in which the heterogeneously catalyzed oxidation (synthesis) 12 takes place to form acrylic acid.

In stage (a) there is obtained however not pure acrylic acid, but a gaseous mixture, which can contain acrylic acid and, as secondary components, substantially unconverted acrolein and/or propene, steam, carbon monoxide, carbon dioxide, nitrogen, oxygen, acetic acid, propionic acid formaldehyde, further aldehydes, and maleic anhydride. In particular, the reaction product mixture typically contains, in wt % based on the total reaction mixture, up to 1% of propene and up to 1% of acrolein, up to 2% of propane, up to 20% of steam, up to 15% of carbon oxides, up to 90% of nitrogen, up to 5% of oxygen, up to 2% of acetic acid, up to 2% of propionic acid, up to 1% of formaldehyde, up to 2% of aldehydes, and up to 0.5% of maleic anhydride.

Stage b

In stage (b) the acrylic acid, and a portion of the secondary components are separated from the reaction gas by absorption with a high-boiling solvents. Suitable for this purpose are all high-boiling solvents capable of absorbing acrylic acid, particularlysolvents having a boiling point above 160° C. Particularly suitable is a mixture of diphenyl ether and biphenyl, such as is commercially available as a mixture of 75wt % of diphenyl ether and 25wt % of biphenyl, also referred to as "diphyl". Advantageously, as shown in FIG. 2, the hot reaction gas obtained from stage (a) after synthesis 12 is fed by means of conduit 47 to a quenching apparatus or a direct condenser K1 where it is cooled by partial evaporating 13 of the solvent prior to said absorption. Particularly suitable for this purpose are venturi scrubbers, bubble-cap columns, or spray condensers. In such case the high-boiling secondary components of the reaction gas from stage (a) condense into the unevaporated solvent (in FIG. 2, the condensation and partial evaporation is designated with reference numeral 13). Furthermore, the partial evaporation of the solvent constitutes a purification step for the solvent. In a preferred embodiment of the invention, a partial stream of the unevaporated solvent, preferably from 1 to 10% of the stream of material that is fed to the absorption column, is removed from the condenser K1 and subjected to solvent purification (not shown). The solvent is distilled over. The solvent distillation serves to avoid an increase in the amount of unwanted substances present in the solvent(s). The high-boiling secondary components, which contain mainly undefined acrylic acid polymers and degradation products of the stabilizers used, remain as residues and are disposed of as secondary components (3) by conduit 33.

The absorption 14 takes place in a countercurrent absorption column K2, which is preferably fitted with sieve, valve, or dual-flow trays, which are subjected to the downward action of (unevaporated) solvent. The gaseous reaction product and optionally evaporated solvent are passed upwardly into the column K2 and are subsequently cooled to the temperature of absorption. In the absorption region of the column K2 both medium-boiling and high-boiling components present in the acrylic acid are removed almost completely from the stream of residual gas.

The remaining, unabsorbed reaction gas of stage (a) is cooled further in order to separate the condensable portion of the low-boiling secondary components thereof, particularly water, formaldehyde and acetic acid, by condensation, shown in FIG. 2 as the acid water quench 15. This condensate is therefore referred to below as acid water. The remaining gas stream, referred to below as recycled gas, mainly consists of nitrogen, carbon oxides and unconverted educts. This is preferably partially recycled to the reaction stages as diluent gas. The recycled gas leaves the absorption column K2 as overheads by conduit 34. Here, the stream is divided, preferably in a ratio of from 3:1 to 1:3 depending on the design of the plant, in particular a ratio of 1:1, where part thereof is recycled by way of conduit 30 to the reactors for synthesis 12 via a gas compressor and the other partial stream is removed by means of ocnduit in the form of the gaseous stream of secondary components (1) to be disposed of. The aforementioned acid water constitutes the secondary components (2) that are dissolved in water and are to be disposed of. This consists of the water that is formed in stage (a) and also water-soluble low-boiling and medium-boiling components, such as acetic acid, formaldehyde, maleic acid etc.

A solvent stream laden with acrylic acid, high-boiling and medium-boiling secondary components and also a small amount of low-boiling secondary components is withdrawn by means of conduit 37 from the absorption region of the column K2 that is used in stage (b) and, in a preferred embodiment of the invention, subjected to desorption with low boiling component stripping 16 and low boiling component wash 17. This is advantageous carried out in a desorption column K3 as shown in FIG. 2, which can preferably be equipped with sieve, valve, or dual-flow trays or alternatively with packing material or well-ordered packings, in the presence of a so-called stripping gas. The stripping gas used can be any inert gas or gas mixture; a gas mixture of air and nitrogen or a partial stream of the recycled gas that is described in (a) is preferably used. During desorption 16 and 17 the major portion of the low-boilers is stripped from the loaded solvent with a portion of the recycled gas withdrawn prior to stage (a) by way of conduit 38, and is recycled to column K2 by way of conduit 39.

A solvent stream that is almost free from low boilers and is loaded with acrylic acid will be withdrawn from the bottoms of the desorption column K3 by way of conduit 41, and is fed to column K4 for distillation.

Stage c

In process stage (c) the acrylic acid is separated from the solvent together with the medium-boiling components and also the final residues of lowboiling secondary components. This separation takes place by means of distillation, for which purpose any distillation column can, basically, be used. To this end a column having sieve trays, dual-flow trays or crossflow sieve trays of metal or having valve trays is advantageous used. In FIG. 2, the distillation is shown with saeveral process steps being solvent mixture distillation 19, medium boiling component distillation 20, low boiling component distillation 21 and partial condensation 22. All these steps are carried out in column K4. In the buoying section of the distillation column K4 the acrylic acid is distilled free from the solvent and the medium-boiling secondary components, such as maleic anhydride (step 21). In order to reduce the low-boiling fraction in the acrylic acid, the acrylic acid is advantageous withdrawn from the column K4 through a side flue 42. This acrylic acid is designated crude acrylic acid. In the stripping section of the column K4 the medium boiling component distillation and the solvent mixture distillation 19 take place. The solvent that is drawn off 20 from the bottom of the column K4 is recycled to the column K2 by way of conduit 43.

At the head of the column K4 a stream that is rich in low-boilers is then withdrawn by way of conduit 44 following condensation 22. Since this stream however still contains acrylic acid, it is advantageously not discarded but recycled to the absorption column K2 and worked up again, as shown in FIG. 2.

The acid water from conduit 36 which can still contain dissolved acrylic acid is preferably treated by extraction with a small partial stream of the solvent that is almost free from acrylic acid coming from the bottom of the distillation column K4 from conduit 40, before it is disposed of in the process of the invention. In this acid water extraction 18 a portion of the acrylic acid is extracted into the solvent and is thus recovered from the acid water. The acid water in turn extracts the polar medium-boiling components from the solvent stream and thus avoids an increase in the level of these components in the solvent circuit. The acid water remaining after extraction is disposed of as the stream of secondary components (2) by way of conduit 45. The solvent being loaded during acid water extraction with acrylic acid is returned via conduit 48 to the solvent stream 43.

It is particularly advantageous to preconcentrate the aforementioned stream of acid water from conduit 45 as far as possible prior to disposal. This can be effected, for example, by using the waste heat which is removed for cooling the reaction gases in the column K2 for the purpose of concentrating the acid water and separating steam. This steam can, eg, be passed to the incinerator plant that is described above via the gaseous stream of secondary components (1). The remaining acid water having a particularly high content of combustible materials yields a particularly large amount of recoverable energy, which can be gained in the form of high-pressure steam. This recovery of energy is particular advantageous, when the steam produced can be used in the plant itself, eg, for the distillation of the acrylic acid in the column K4 or in the solvent distillation and for driving the compressors for air and/or recycled gas by means of steam turbines.

The crude acrylic acid that is obtained in stage (c) contains, based, in each case, on the crude acrylic acid, preferably from 98 to 99.8 wt %, particular from 98.5 to 99.7 wt %, of acrylic acid and from 0.2 to 2 wt %, particularly from 0.5 to 1.5 wt % of impurities such as acetic acid, aldehydes, and maleic anhydride. This acrylic acid can, if the demands on its purity are not very high, optionally be used as it is for an esterification. Further separation of the secondary components of the thus isolated crude acid, if necessary, can optionally take place by crystallization, distillation or other suitableseparating methods, according to the quality of acrylic acid required. The acrylic acid thus obtained can either be directly processed further or be subjected to further chemical reactions such as esterification.

The invention is explained in detail with reference to the following example, which represents a preferred embodiment.

The following statements refer to a plant for the production of acrylic acid, which is operated according to the process described in DE-A-2 136 396, where the product containing acrylic acid is absorbed following synthesis in a high-boiling solvent consisting of 80 wt % of diphyl (mixture of diphenyl ether and diphenyl) and 20 wt % of dimethylphthalate (DMP). The reaction scheme substantial corresponds to the process illustrated in FIG. 2, wherein to simplify matters, columns/apparatus K1 to K4 are mentioned only.

From a synthesis section, which consists of three cascades of reactors each having two tube bundle reactors acting as oxidation reactors, there is obtained, as reaction product, a gas stream composed, on the average, of the following components in percentages by weight:

| | |
|---|---|
| acrylic acid | 9.3% |
| $CO_2$ | 3.2% |
| nitrogen | 77.4% |
| oxygen | 3.7% |
| water | 3.8% |

The following statements refer in each case to this stream of reaction gas, which is referred to below as the "crude product".

This crude product is mixed in a prequench (direct condenser) K1 with 10 kg of diphyl/DMP per m³(STP) of crude product, as solvent, and is afterwards passed to the absorption column K2 at a gas temperature of approximate 170° C. Further processing takes place as described above.

A small side stream of the solvent in the bottoms of the absorption column K2 of from 0.5 to 1 wt % of the amount that is pumped through the column K1 is withdrawn and subjected to flash evaporation in the solvent purification where T is equal to 150° C. to 200° C. and p is equal to from 500 to 200 mbar. In this case the distillate produced is a pure solvent, whereas the bottoms comprise a product side stream which is disposed of as the stream of secondary components (3). The elementary composition of this stream of secondary components (3) is, on average:

| | |
|---|---|
| C | 68.8% |
| H | 4.4% |
| O | 23.1% |
| N | 1.05% |
| S | 2.2% |

In this case the amounts of nitrogen and sulfur are derived from the process stabilizer used, ie phenothiazine, which is added in the distillation column K4 and which also passes into the absorption column K2 due to the circulation of the solvent. The stream of secondary components (3) is a blackish, solid to viscous material having a solidifying point of approximately 100° C.

The components of the crude product that are not condensed in the absorption column K2 (inert gases, low-boiling organic contents, water CO, $CO_2$ etc.) are recycled to the reactors as "recycled gas", of which a partial stream is branched off and fed to the combustion zone as a stream of secondary components (1). This branched off partial stream consists of 90 wt % of nitrogen, 4 wt % of oxygen, 4 wt % of CO and $CO_2$, 1 wt % of water, and 1 wt % of organic components. A further partial stream of the recycled gas is used for stripping low-boilers from the solvent stream containing acrylic acid in the column K3. This stream of recycled gas now enriched with low-boiling components is likewise recycled to the absorption column in order to appear again at the end of this absorption column K2 in the partial stream of the recycled gas, or in the partial stream fed to the combustion zone.

The stream of material leaving the absorption column K2, is stripped in the nextstep with the partial stream of the recycled gas described above in a desorption column K3. Now substantially feed from low boilers, the stream of product and solvent passes to the distillation column k4, where the product is removed through a side flue. The high-boiling solvent then returns to the absorption column K2 at the bottom. The low-boiling fractions that are formed at the top of the column K4 and in the top condenser are likewise recycled to the absorption column K2. All of the water (acid water) that present in the upper cooling circuit of the absorption column K2 is fed to the combustion zone as a stream of secondary components 2 following extraction with recycled solvent. The same applies to the removed partial stream of the recycled gas, which forms the stream of secondary components 1.

Burning of the streams of secondary components that are to be disposed of takes place in a burner of the flame evaporating burner type, as is shown in FIG. 1. The individual streams of material come into contact with each other in the combustion chamber, the feed of these streams of material being effected through concentric annular outlets. In additional to the streams of secondary components named above, which are to be disposed of, there must also be added: support gas (preferably natural gas), air for combustion, and atomizing air.

The waste heat section of the combustion chamber is thus constructed in such a manner that the hot exhaust gases are fist of all utilized for the production of high-pressure steam and are then used for superheating this steam under a pressure of 21 bar. Afterwards the hot exhaust gases are used in the second stage of the two stages involved in preheating the stream of secondary components (1) to be disposed of, for combustion, afterwards they heat the air for combustion, and then, as a penultimate step, they supply energy to the first of the two stages involving preheating of the stream of secondary components (1). The rest of the energy is used for the production of low-pressure steam according to plant settings. This means that the energy recovered in the plant can be measured in terms of the amount of steam that is produced. In this plant there were carried out two experiments according to the process of the invention, the stream of secondary components (3) being externally disposed of in the first experiment, whilst it was burnt with the other secondary components in the second experiment.

Experiment 1

Residues having the following composition, based in each case on the crude product:
gaseous stream of secondary components (1) 38.5% v/v
liquid aqueous stream of secondary components (2) 3.7% w/w
liquid pasty organic stream of secondary components (3) 0.3% w/w
was disposed of by burning the gaseous and liquid aqueous streams (1) and (2) until free from residue and disposing of the stream of components 3 externally.

During burning the temperature at the end of the combustion chamber was approximately 904° C. An increase in the production of high-pressure steam by 22.4% compared with a blank experiment, which was carried out using support
gas instead of the streams of secondary components to be disposed of, was found.

Experiment 2

Residues having the following composition, based in each case on the crude product:
gaseous stream of secondary components (1) 38.50% v/v
liquid aqueous stream of secondary components (2) 3.7% w/w
liquid pasty organic steam of secondary components (3) 0.4% w/w
were disposed of by feeding all three streams of material to the burner system described above. Since in this case the stream of secondary components 3 was also burnt with the other steams, a nozzle having a further annular feed gap was used in the burner system.

There was found to be an increase in steam generation of 24.6% compared with the blank experiment (burning with support gas only).

The present experiments thus show that the process of the invention provides for the residue-free disposal of streams of secondary components that are formed during the preparation of acrylic acid.

What is claimed is:

1. A process for the disposal of secondary components, said secondary components being formed during preparation of (meth)acrylic acid, said process comprising:
   (1) combusting a gaseous low-boiling secondary component in a combustion stage; and
   (2) feeding an aqueous solution of a low- or medium-boiling secondary component to said combustion stage, wherein said low-boiling secondary component possesses a lower boiling point than (meth)acrylic acid and said medium-boiling secondary component possesses approximately the same boiling point as (meth)acrylic acid, and wherein said preparation of (meth)acrylic acid comprises:
(a) catalytically oxidizing propene, isobutene, acrolein, methacrolein, or a mixture thereof in a gas phase;
(b) absorbing a reaction product that is formed in step (a) in a solvent, to obtain a loaded solvent; and
(c) separating acrylic acid or methacrylic acid from said loaded solvent of step (b) by extraction or distillation or both.

2. The process of claim 1, wherein said low-boiling secondary component comprises a compound selected from the group consisting of carbon monoxide, carbon dioxide, nitrogen, acrolein, acetaldehyde, propane, propene, formaldehyde, formic acid, isobutene, methacrolein, and mixtures thereof.

3. The process of claim 1, wherein said aqueous solution of a low- or medium-boiling secondary component comprises a compound selected from the group consisting of acetic acid, maleic acid, fumaric acid, formaldehyde, propionic acid, benzaldehyde, diacrylic acid, hydroxypropionic acid, benzoic acid, diphenyl ether, and mixtures thereof.

4. The process of claim 1, wherein said low-boiling secondary component comprises a compound selected from the group consisting of carbon monoxide, carbon dioxide, nitrogen, acrolein, acetaldehyde, propane, propene, formaldehyde, formic acid, isobutene, methacrolein, and mixtures thereof, and wherein said aqueous solution of a low- or medium-boiling secondary component comprises a compound selected from the group consisting of acetic acid, maleic acid, fumaric acid, formaldehyde, propionic acid, benzaldehyde, diacrylic acid, hydroxypropionic acid, benzoic acid, diphenyl ether, and mixtures thereof.

5. The process of claim 4, wherein said aqueous solution of a low- or medium-boiling secondary component comprises a compound selected from the group consisting of acetic acid, maleic acid, fumaric acid, formaldehyde, and mixtures thereof.

6. The process of claim 4, wherein said aqueous solution of a low- or medium-boiling secondary component comprises 0.1 to 10 wt % of acetic acid, 0.0 1 to 5 wt % of maleic acid, 0.01 to 8 wt % of fumaric acid, and 0.2 to 4 wt % of formaldehyde, based on the total weight of said secondary component.

7. The process of claim 1, wherein said low- or medium-boiling secondary component is fed to said combustion stage together with a high-boiling secondary component which has been treated with a low viscosity solvent, wherein said high-boiling secondary component possesses a higher boiling point than (meth)acrylic acid.

8. The process of claim 7, wherein said high-boiling secondary component comprises a compound selected from the group consisting of acrylic acid polymers, methacrylic acid polymers, phenothiazine, p-nitrosophenol, methylene blue, and mixtures thereof.

9. The process of claim 7, wherein said high-boiling secondary component comprises an acrylic acid polymer or a methacrylic acid polymer.

10. The process of claim 7, wherein said low-boiling secondary component comprises a compound selected from the group consisting of carbon monoxide, carbon dioxide, nitrogen, acrolein, acetaldehyde, propane, propene, formaldehyde, formic acid, isobutene, methacrolein, and mixtures thereof; wherein said aqueous solution of a low- or medium-boiling secondary component comprises a compound selected from the group consisting of acetic acid, maleic acid, fumaric acid, formaldehyde, propionic acid, benzaldehyde, diacrylic acid, hydroxypropionic acid, benzoic acid, diphenyl ether, and mixtures thereof; and wherein said high-boiling secondary component comprises a compound selected from the group consisting of acrylic acid polymers, methacrylic acid polymers, phenothiazine, p-nitrosophenol, methylene blue, and mixtures thereof.

11. The process of claim 10, wherein said aqueous solution of a low- or medium-boiling secondary component comprises a compound selected from the group consisting of acetic acid, maleic acid, fumaric acid, formaldehyde, and mixtures thereof.

12. The process of claim 10, wherein said aqueous solution of a low- or medium-boiling secondary component comprises 0.1 to 10 wt % of acetic acid, 0.01 to 5 wt % of maleic acid, 0.01 to 8 wt % of fumaric acid, and 0.2 to 4 wt % of formaldehyde, based on the total weight of said secondary component.

13. The process claim 7, wherein said low viscosity solvent has a viscosity of $0.5 \times 10^3$ to $2 \times 10^3$ Pa·s.

14. The process claim 7, wherein said low viscosity solvent has a boiling point of 100° C. to 250° C.

15. The process claim 7, wherein said low viscosity solvent is selected from the group consisting of acetone, dimethyl formamide, pentane diol, hexane diol, glycerol, glycol, dimethyl glycol, monomethyl glycol, monoethyl glycol, diethyl glycol, and mixtures thereof.

16. The process of claim 15, wherein said low-boiling secondary component comprises a compound selected from the group consisting of carbon monoxide, carbon dioxide, nitrogen, acrolein, acetaldehyde, propane, propene, formaldehyde, formic acid, isobutene, methacrolein, and mixtures thereof; wherein said aqueous solution of a low- or medium-boiling secondary component comprises a compound selected from the group consisting of acetic acid, maleic acid, formaldehyde acid, formaldehyde, propionic acid, benzaldehyde, diacrylic acid, hydroxypropionic acid, benzoic acid, diphenyl ether, and mixtures thereof; and wherein said high-boiling secondary component comprises a compound selected from the group consisting of acrylic acid polymers, methacrylic acid polymers, phenothiazine, p-nitrosophenol, methylene blue, and mixtures thereof.

17. The process of claim 16, wherein said aqueous solution of a low- or medium-boiling secondary component comprises a compound selected from the group consisting of acetic acid, maleic acid, fumaric acid, formaldehyde, and mixtures thereof.

18. The process of claim 16, wherein said aqueous solution of a low- or medium-boiling secondary component comprises 0.1 to 10 wt % of acetic acid, 0.01 to 5 wt % of maleic acid, 0.01 to 8 wt % of fumaric acid, and 0.2 to 4 wt % of formaldehyde, based on the total weight of said secondary component.

19. The process of claim 1, wherein said combusting is carried out in a combustion chamber using a support gas burner or multifuel burner.

20. The process of claim 1, wherein said combusting is carried out at a temperature of from 800° C. to 1000° C.

21. The process of claim 1, wherein natural gas and/or air are additionally fed to said combustion stage.

* * * * *